United States Patent [19]

Gale et al.

[11] Patent Number: 4,827,776
[45] Date of Patent: May 9, 1989

[54] HAY SAMPLING DEVICE

[76] Inventors: Jody A. Gale, 595 E. 400 North; Jim L. Bushnell, 2060 N. 1400 East, both of Logan, Utah 84321

[21] Appl. No.: 894,645

[22] Filed: Aug. 8, 1986

[51] Int. Cl.$^4$ .................................................. G01N 1/08
[52] U.S. Cl. .................................. 73/864.45; 408/208
[58] Field of Search ........... 73/864.45, 864.44, 864.43; 175/308, 403; 408/67, 204, 206, 208

[56] References Cited

U.S. PATENT DOCUMENTS

| | | | |
|---|---|---|---|
| 408,223 | 8/1889 | Draper | 73/864.45 |
| 473,316 | 4/1892 | Hunter | 73/864.45 |
| 2,564,451 | 8/1951 | Sandberg et al. | 408/206 |
| 2,666,330 | 1/1954 | McAndrew | 73/864.44 |
| 2,853,904 | 9/1958 | Mackey | 408/206 |
| 2,955,805 | 10/1960 | Jones, Jr. et al. | 175/403 X |
| 3,016,749 | 1/1962 | Wollner . | |
| 3,064,482 | 11/1962 | Wollner . | |
| 3,081,635 | 3/1963 | Bowers | 73/864.44 |
| 3,110,184 | 11/1963 | Gructzmen | 73/864.45 |
| 3,921,459 | 11/1975 | Willett . | |
| 4,096,749 | 6/1978 | Stewart | 73/864.45 |
| 4,179,929 | 12/1979 | Redding | 73/864.45 X |
| 4,516,438 | 5/1985 | Hodge | 73/864.44 |
| 4,539,750 | 9/1985 | Jones et al. | 408/204 X |
| 4,696,308 | 9/1987 | Meller et al. | 408/204 X |

FOREIGN PATENT DOCUMENTS

| | | | |
|---|---|---|---|
| 152560 | 2/1951 | Australia | 73/864.43 |
| 398859 | 9/1973 | U.S.S.R. | 73/864.44 |
| 465575 | 6/1975 | U.S.S.R. | 73/864.45 |
| 524096 | 11/1976 | U.S.S.R. | 73/864.45 |
| 832394 | 5/1981 | U.S.S.R. | 73/864.45 |

OTHER PUBLICATIONS

"Good Sample Impossible Without Probe," Dairy, p. 12 (Nov. 1985).
Advertisment, "New Hay Sampling Tool Makes Sampling Easier, E-Z Prob," Holstein World, p. 73 (Feb. 10, 1986).
Catalog Listing and Instruction Sheets, "Penn State Forage Sampler" (date unknown), but by Nov. 1986; 3 pages, Scientific Systems Inc., State College, PA.
Advertisements, "A Better Way to Sample Hay! . . . E-Z Probe Forage Sampler" (dates unknown), but by Nov. 1986; 2 pages, by Northwest AG Consultants of Culves, OR.
Advertisement, "Northwest AG's Forage Probe" (date unknown), but by Nov. 1986; 7 pages; by Northwest AG Consultants of Culver, Oregon.

Primary Examiner—Tom Noland
Attorney, Agent, or Firm—Workman, Nydegger & Jensen

[57] ABSTRACT

A device for obtaining a sample from a volume of hay. The device is provided with a hollow tube member having an intake end and a discharge end. The interior diameter of the hollow tube is at a minimum at the intake end. The intake end is also provided with a re-sharpenable and serrated cutting edge positioned about the perimeter of the intake end of the hollow tube. A spiral ridge is provided on the exterior of the hollow tube member in proximity to the intake end. In use, the intake end of the hollow tube is inserted into a volume of hay, such as a bale, roll, or stack, and the hollow tube is rotated. The spiral threads engage the volume of hay and the user of the device may selectively rotate the hollow tube such that it is drawn into the hay or withdrawn from the hay. The hay cores which are gathered into the hollow tube are collected in a collection container attached to the hollow tube member. The hollow tube member may be rotated by means of a hand brace operated by the user or by means of a power rotation implement.

12 Claims, 3 Drawing Sheets

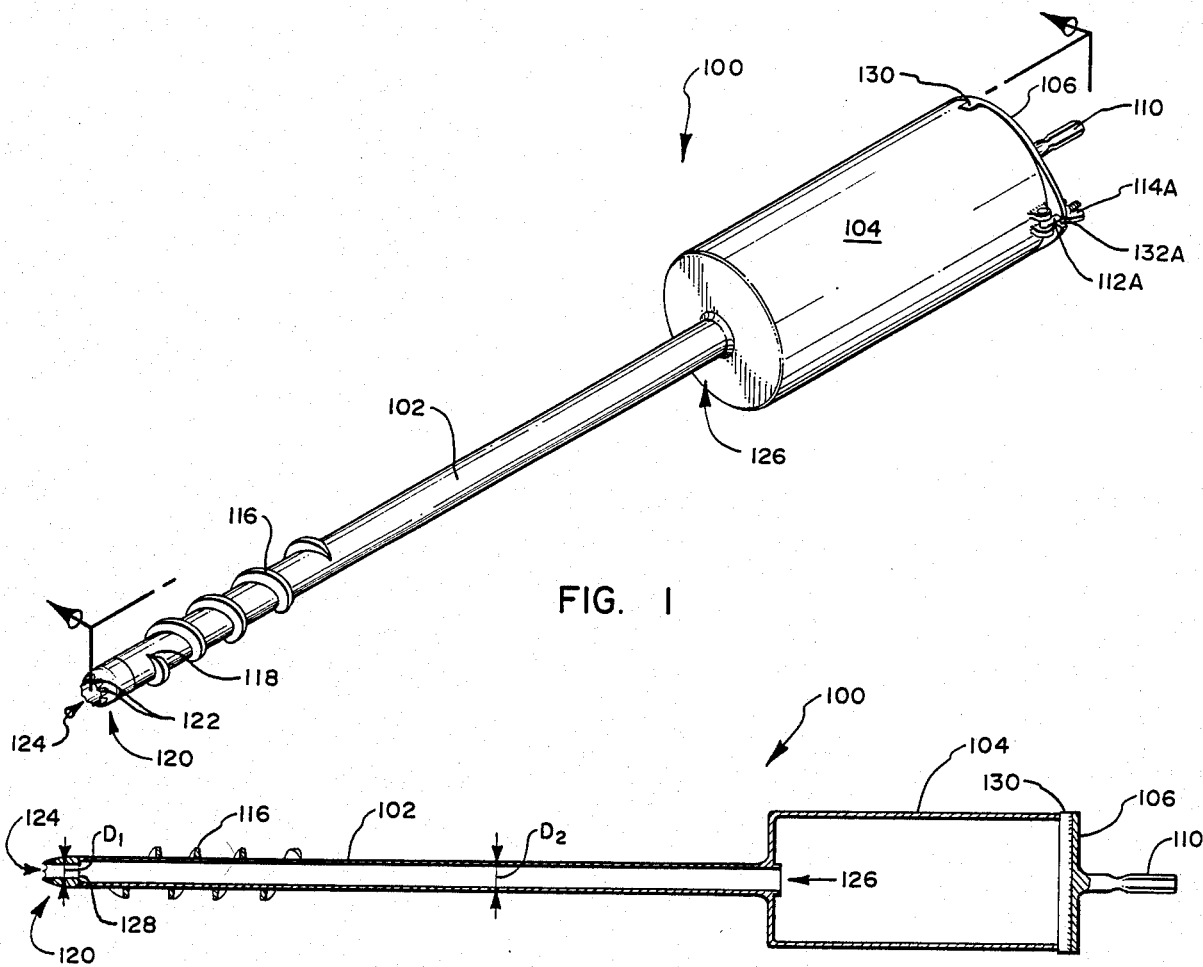
FIG. 1
FIG. 2
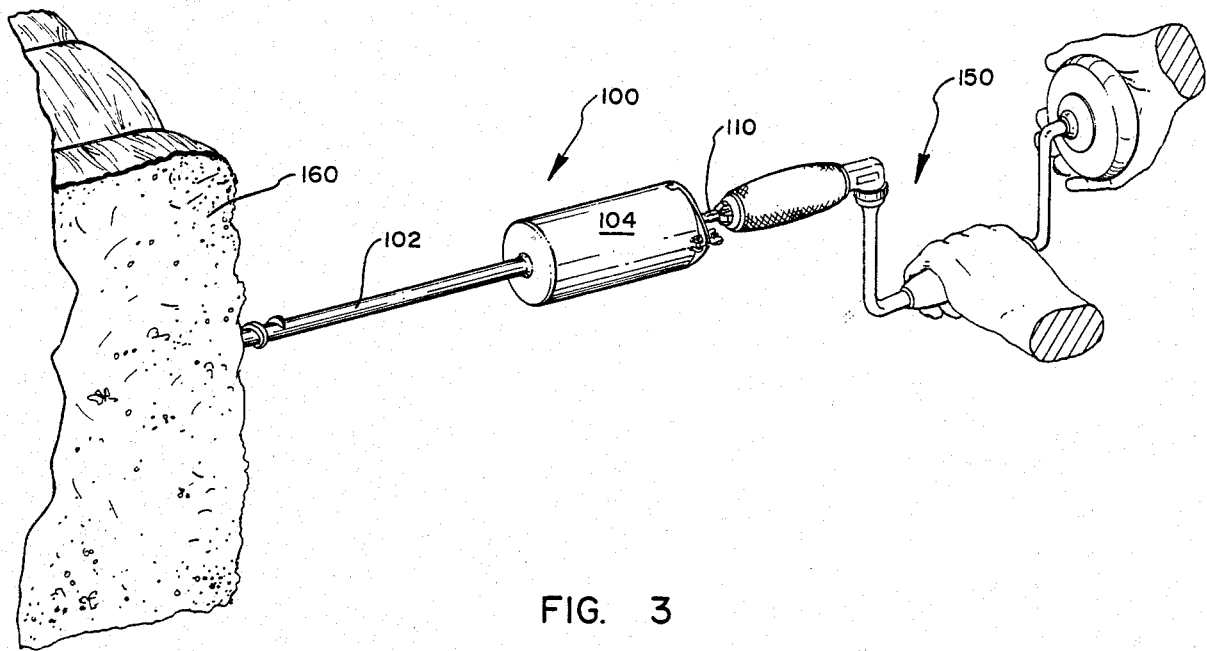
FIG. 3

HAY SAMPLING DEVICE

BACKGROUND

A. Field of the Invention

The present invention relates to devices for obtaining samples of harvested forage. More particularly, the present invention is directed to a device for obtaining a sample of a volume of hay which is loose or which has been baled, rolled, or stacked.

B. The Prior Art

The raising of livestock for both food and fiber is an important industry throughout the world. While it is sometimes the case that livestock are raised on open range land or open pasture, it is becoming increasingly important to modern agriculture that forage be harvested and stored for later use, particularly during the colder winter months. Also, due to the increased specialization of modern agriculture, and with livestock often being located a significant distance away from a source of forage, it is important to be able to conveniently store and transport forage.

Forage may be defined as any agricultural crop which is used for feeding livestock. Forage may be stored as silage, which is the feed resulting from the storage and fermentation of green wet crops under anaerobic conditions. Alternatively, forage may be stored as hay, which is the above ground part of a stemmed forage crop which is stored in dry form for later feeding to livestock.

Many different forages may be stored as hay. Such forages may include legume plants such as red clover, alsike clover, lespedeza, sericca, and alfalfa. Of the above listed legumes, alfalfa is by far the most commonly grown in the midwestern and western portions of the United States. Nonlegume plants that are stored as hay include coastal bermuda grass, Timothy grass, red top grass, bromegrass, orchard grass, and many other nonlegume forages.

All of the above forages are generally cut and then dried into hay as they lay in the field. The object in making hay is to reduce the moisture content of green forage crops sufficiently to permit their safe storage without spoilage or serious loss of nutrients. Generally, the maximum permissible moisture content for hay at the time of baling is in the range of from about eighteen percent (18%) to about twenty-two percent (22%), depending upon a variety of factors.

It is important to properly harvest and dry the hay before it is stored. Freshly mown hay which is stored before it is sufficiently dry can be destroyed by fire resulting from spontaneous combustion. Hay which is stored containing excessive moisture may also tend to mold, making it unsuitable for feed purposes. Furthermore, hay which is improperly harvested may suffer from a loss of nutritional value due to the loss of leaves, the most nutritious part of the hay.

The time of harvesting, even when varying by one day, may make a significant difference in the nutritional content of the hay. Presently, it is common to store hay in the form of bales, rolls, or as a stack which is a relatively large "loaf-like" compressed form.

Of course, the reason hay is stored and fed to livestock is to provide the livestock with proper amounts of nutrition and roughage. As suggested earlier, the nutrition of various volumes of hay may vary greatly from one volume to the next even when the hay is harvested from the same field. Again, the time of harvest, weather conditions, and harvesting techniques all have an impact on the nutritional value of the hay.

It is important for the owner of livestock to know the nutritional content of the particular hay which is being fed to the livestock. If the hay is low in a particular nutrient, supplements may need to be added to form a balanced ration so that the growth of the livestock is not retarded. Knowing the nutritional value of the hay being fed to dairy cattle is particularly important since dairy cattle will not produce the maximum possible amount of milk unless provided with proper nutrition.

Beef cattle also require a balanced ration for maximum growth. Since meat is sold by the pound, the proper growth of the beef cattle, or other livestock, has a great impact on the income and profitability of any livestock operation. Still further, individuals engaged in the production of hay for sale to others receive a higher price for hay which is more nutritious than less desirable hay. Thus, there is an acute need to know the nutritional content of the hay that is being fed to the livestock.

Generally, a minimal nutritional analysis of hay will specify the content of the hay in the following categories: moisture; crude protein; crude fats; crude fiber; nitrogen free extract; and mineral matter or ash. Furthermore, it may be desirable to determine the amounts of minerals and vitamins in the hay sample.

Often a farm is devoted nearly exclusively to the production of hay, generally alfalfa in the western United States, which is to be sold to others. In such a case, both the owner of the livestock buying the hay, and the farmer selling the hay, desire to know the nutritive content of the hay so that a fair price may be established. However, as indicated earlier, it is necessary to determine the nutritive content of particular volumes of hay to be sold since the time and method of harvesting may dramatically affect the nutritive content.

As indicated earlier, if the hay is stored in bales it would be desirable to learn the actual nutritive content of each bale of hay. However, since this is not practical, it is necessary to rely on taking random samples of the hay and assume that the resulting combined sample is representative of the nutritive value of the hay to be sold or fed.

Because of the variations in nutritive value, very unacceptable results are obtained when only three or four bales out of, for example, 1,000 bales of the hay are used in the sample. Likewise, obtaining perhaps 50 "grab samples" by randomly pulling "chunks" of hay from the surface of 25 bales is also unacceptable. Merely pulling a "chunk" of hay from the surface of the bale often causes the leaves to fall from the stems, the leaves being the most nutritious part of the hay, thus causing the hay to appear low in nutritive value when analyzed. Also, the hay on the outer surface of a bale may be of lower nutritive value, due to exposure to the sun and weather, than the hay in the interior of the same bale.

In many cases, the misinformation obtained by poor sampling techniques is more misleading than if the hay were just assumed to be "average". It has been found that the best method of obtaining a sample of hay for nutritional analysis is to obtain a sample which includes many small cores taken from several bales, the cores including material from the outer surface of the bale's butt end to nearly the middle of the bale.

Due to the critical need to obtain an accurate sample of hay for nutritional analysis, those skilled in the art have long felt a need for a device which allows the obtaining of such a sample while not seriously disrupting the volume of hay, such as a bale. In recent years, the convenience of making, as well as the accuracy of, nutritional analysis of hay has increased due to new techniques and testing devices. However, the accuracy of any analysis is severely limited by whether or not the sample used for the analysis is representative of the hay to be sold or fed. In an effort to satisfy this long felt need, many devices have been produced.

One type of device for sampling hay which is found in the prior art for sampling hay is disclosed in U.S. Pat. No. 4,516,438 to Hodge (the Hodge patent). The hay probe disclosed in the Hodge patent includes a pair of heavy duty handles which are mounted on the side of a hollow elongated straight probe. A glass jar is attached to the end of the probe so that the material entering the probe is deposited into the glass jar.

When using the device disclosed in the Hodge patent, the user grasps the handles and, sometimes with a great deal of effort, attempts to push or plunge the hollow probe as far as possible into the hay. Many times bales of hay are very tightly packed, thus creating an efficient ratio of weight of the bale to the size of the bale for storage and transportation, but also making insertion of such a probe extremely difficult. Such difficulty during insertion and removal of the probe is often referred to as binding. Still further, in the device disclosed in the Hodge patent, the hollow tube may become plugged with the hay core which is being obtained. Use of such probes as disclosed in the Hodge patent may often times be so difficult that the user will quickly fatigue and thus decide to obtain, for example, only five cores rather than the recommended twenty cores which may be necessary for a statistically accurate sample for analysis.

Other devices available in the art improve somewhat on the device disclosed in the Hodge patent. For example, one device, manufactured by Northwest AG Consultants, Inc. of Culver, Oreg., incorporates a knife edge around the open perimeter of the hollow probe. A further improvement includes the use of a hand brace (of the type sometimes used by carpenters to drill holes in a board) which may be attached to the probe. Devices which are intended to be used with hand braces include those manufactured by Forageuers, Inc. of Minneapolis, Minn. and Northwest AG Consultants, Inc. By use of a hand brace, the user is allowed to, still with some difficultly, rotate the probe thus decreasing the relative effort required to insert the probe into the bale.

Still further, in an attempt to reduce the effort that must be expended by the user and thus also the resulting fatigue, some devices are available which allow the replacement of a hand brace with an hand-held electric motor. These devices include those available from Nasco West of Modesto, Calif., and Oakfield Apparatus, Inc. of Oakfield, Wis.

However, the requirement of a power supply for the electric motor often discourages use of such power operated devices, in addition to their added weight, cost, and complexity. Also, if a power operated device should bind within a bale, the user may suffer an injury, for example, a sprained wrist. Thus, a hay sampling device should be easily operable manually or alternatively, safely operated by an electric motor for those occasions where a power supply is readily available.

As will be appreciated from the foregoing discussion, obtaining a representative sample of hay from a plurality of bales, rolls, or stacks has been a problem faced by those skilled in the present art for a long time. As evidenced by the attempts found in the prior art, many skilled in the art have searched for a solution to the long felt need for a device to assist in obtaining a representative sample of hay.

In view of the foregoing problems found in the prior art, it would be a significant advance in the art to provide a hay sampling probe which may be easily and efficiently inserted into, and withdrawn from, a bale, roll, or stack of hay by a single user. It would also be beneficial to provide a hay sampling probe which is resistant to binding and plugging of the probe while the sample is being taken.

BRIEF SUMMARY AND OBJECTS OF THE INVENTION

The present invention is directed to a device to obtain a sample from a volume of hay. The apparatus of the present invention is provided with a hollow tube member, or cylinder, which is generally elongated. The hollow tube member may be exchanged for another tube member of a different length. The perimeter of the intake end of the tube is provided with a resharpenable cutting tip. The cutting tip is preferably removable in case of damage to the tip. The cutting tip is provided with a serrated cutting edge to improve the cutting efficiency. The interior diameter of the tube is at a minimum at the intake end which reduces the occurrences of jamming of the hay core within the tube.

The exterior of the sampling tube is provided with a spiral ridge, also referred to as a spiral thread. The spiral ridge preferably begins in proximity to the intake end and extends some distance along the tube. The spiral ridge serves as a screw apparatus allowing the tube to be drawn into or withdrawn from the volume of hay as the apparatus is rotated. The structure and length of the spiral ridge may be varied according to the length of the hollow tube member and whether the device is power or hand operated. The spiral ridge serves an important function in the efficient operation of the device.

To obtain a hay core the intake end of the hollow tube is inserted into the volume of hay as it is rotated by the operator. The rotation of the tube causes the spiral threads to engage the volume of hay. As rotation of the tube is continued, the spiral threads draw the tube into the volume of hay. As the tube is drawn into the volume of hay, a hay core is cut and gathered into the interior of the hollow tube.

The hay core which is contained in the hollow tube may be discharged into a collection container attached to the hollow tube. The collection container may hold many individual cores making up the sample to be analyzed. The contents of the collection container may, at a later time, be transferred to a suitable container for transportation to the location where analysis of the hay will be made. Alternatively, the hay core may be directly transferred from the hollow tube to another suitable container.

In view of the foregoing, it is a primary object of the present invention to provide a hay sampling device which more accurately and efficiently collects hay samples than those devices and methods previously available in the art.

Another object of the present invention is to provide a hay sampling device which may be repetitively used by a single user for obtaining many cores without causing the user to become fatigued or tired.

Another object of the present invention is to provide a hay sampling device with a plurality of hollow tubes which are of different lengths thus allowing cores to be taken from various sized of volumes of hay.

Still another object of the present invention is to provide a hay sampling device with a resharpenable cutting tip which is conveniently replaceable in case the cutting tip becomes dull or damaged.

Another object of the present invention is to provide a hay sampling device which is particularly suited for either power driven operation or hand driven operation.

Yet another object of the present invention is to provide a hay sampling device which requires a minimum of effort from the operator during both the insertion and withdrawal of the device thus reducing operator fatigue and frustration.

It is another object of the present invention to provide a hay sampling device which includes a collection container for receiving the hay core gathered in the interior of the hollow tube.

Yet another object of the present invention is to provide a hay sampling device whose structure reduces the occasions of the hay core becoming plugged within the interior portion of the device.

Still another object of the present invention is to provide a hay sampling device which is provided with a container for conveniently collecting a number of individual cores making up the sample.

These and other objects of the present invention will become apparent from the following description of the preferred embodiments taken in connection with the accompanying drawings.

BRIEF DESCRIPTION OF THE DRAWINGS

FIG. 1 is a perspective view of one presently preferred embodiment of the present invention.

FIG. 2 is a cross-sectional view of the embodiment illustrated in FIG. 1.

FIG. 3 is a perspective view showing the embodiment illustrated in FIG. 1 being used to obtain a hay core from a volume of hay.

DETAILED DESCRIPTION OF THE PREFERRED EMBODIMENTS

Figure 4:
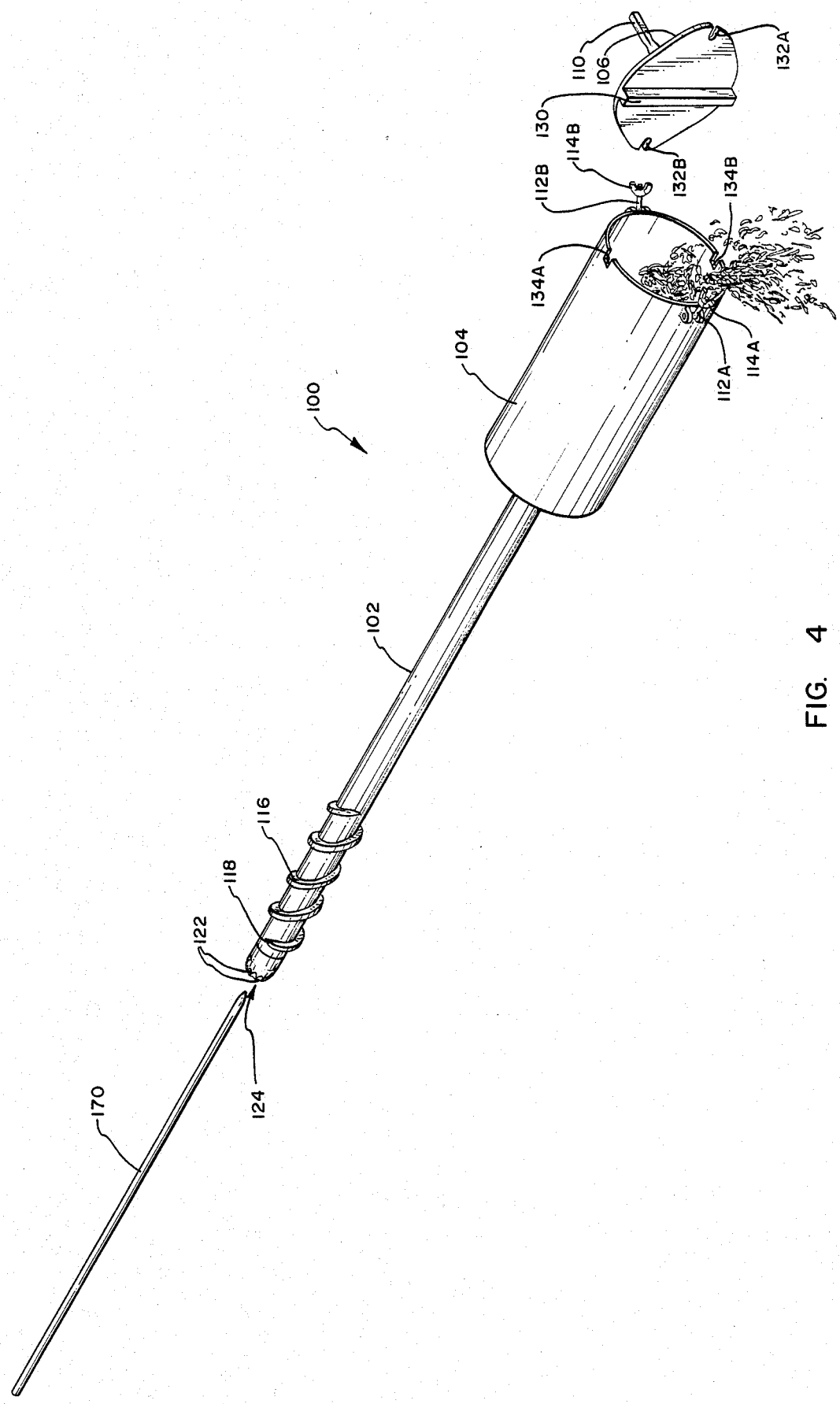
FIG. 4 is a perspective view of the embodiment illustrated in FIG. 1 showing the hay samples being removed from the device.

Reference will now be made to the drawings wherein like structures are designated by like numerals throughout. One presently preferred embodiment of the hay sampling device of the present invention is generally designated 100 in FIGS. 1-4. The embodiment illustrated in FIG. 1 generally comprises a hollow tube member 102, also referred to as an elongated cylinder or probe 102, and a collection container 104, or collection cup 104.

As used in this specification and the claims appended hereto, the phrase "volume of hay" is intended to mean a bale, roll, stack, or any other structure or arrangement which is presently used, or which may be devised in the future, to store or transport hay. Furthermore, the phrase is also intended to encompass a pile of loose hay.

In use, hollow tube member 102 is inserted into a volume of hay such that a hay core is received into the hollow portion of tube member 102 to be collected in collection container 104 and ultimately removed from collection container 104 for analysis. The remaining structures of the device shown in the drawings greatly assist the user of the device in properly operating, with ease, the illustrated embodiment in order to obtain an accurate and representative sample of hay.

The term "core", as used in this specification and the claims appended hereto, shall refer to the hay received into the hollow portion of the tube member 102 each time the tube member 102 is inserted into a volume of hay. Furthermore, the term "sample" shall refer to a plurality of cores which have been obtained.

In the case of baled hay, it is generally recommended that 20 cores be taken from the butt end of 20 bales chosen at random for about every 50 tons of hay in order to obtain a statistically accurate sample. In the case of rolled hay, it may be necessary to take several cores from various locations in the roll in order to obtain a representative sample. Taking cores from the butt end of a bale helps avoid obtaining a nonrepresentative sample by taking a core through only a portion of the bale dominated by a patch of weeds. Similar considerations must be kept in mind when taking cores from rolls, stacks, or piles of hay in order to obtain a representative sample.

Hollow tube member 102 of embodiment 100 may generally be constructed of steel. One preferred material from which tube member 102 is fabricated is a hot rolled steel tubing. Likewise, the remaining structures of the embodiment shown in the figures may also be constructed of steel. The considerations to be given credence when choosing materials for tube member 102, as well as the remaining structures, include: strength, rigidity, and resistance to corrosion and rust. If the materials chosen are not particularly resistant to corrosion and rust, it may be necessary to take steps to prevent any rust or corrosion which occurs from contaminating the sample and thus providing inaccurate analysis of the nutritional value of the hay. Also, both the interior and exterior surfaces of tube member 102 should be smooth to reduce any chance of the hay plugging the tube.

The length of tube member 102 is preferably in the range of from about seven inches to about twenty-four inches for use with hay bales common in the industry. In the embodiment illustrated in FIGS. 1-4, tube member 102 is preferably about 18 inches in length. However, it will be appreciated that the length of tube member 102 may vary greatly according to the particular application.

Since it is best to take a sample from the butt end of a bale, tube member 102 should be long enough to reach nearly to the middle of the bale. Taking the sample from the butt end provides easy operation of the device, the most accurate sample as mentioned earlier, and the least disruption of the bale of hay. Also, a device to be used for obtaining samples of very large stacks of hay may require tube member 102 to be four feet or longer.

Tube member 102 is provided with a cutting tip, generally designated 120 in FIGS. 1 and 2. As can be seen best in FIG. 1, the presently preferred embodiment incorporates serrations 122 into cutting tip 120. Cutting tip 120 is preferably fabricated from a hardened steel which may be ground to a sharp edge.

As can be seen best in the cross-sectional view of FIG. 2, cutting tip 120 is welded to the tube 104, the seam being shown at 128. The exterior diameter of cutting tip 120 substantially matches the interior diameter of tube member 102, as can be seen in FIG. 2. It is important that the exterior diameter of tube member 102 not be too large or excessive effort may be required to insert the device into the volume of hay. The exterior diameter may be in the range from about ⅜ inch to about 1½ inches. It is preferred that the exterior diameter be about ⅝ inch. Intake end 124 of cutting tip 120 is tapered to a cutting edge which is provided with serrations 122. Serrations 122 greatly assist with the cutting of the hay.

It will be appreciated that many structures other than those shown in FIGS. 1–4 may be used to form cutting tip 120. For example, cutting tip 120 may be removable as will be explained shortly. Furthermore, the materials which form cutting tip 120 should preferably be a steel which may be conveniently resharpened by the user. Since cutting tip 120 may become dull through use or damage, allowing the user to resharpen cutting tip 120 is a great advantage insofar as the need for replacing cutting tip 120 is reduced or eliminated.

As shown in FIG. 2, the interior diameter of cutting tip 120 is indicated by arrows and the line marked $D_1$ in FIG. 2. The interior diameter of tube member 102 is also marked by arrows and the line designated $D_2$ in FIG. 2. Diameter $D_1$ is preferably in the range from about ¼ inch to about 3/4 inch. Furthermore, the diameter indicated at $D_2$ is preferably in the range from about 5/16 of an inch to about 1¼ inches. In the embodiment illustrated in FIGS. 1–4, it is preferred that $D_1$ be about 7/16 of an inch and $D_2$ be about 9/16 of an inch.

It should be appreciated that if the interior diameters of hollow tube 102 and cutting tip 120 are too large, the cores taken, and the resulting sample, will be too large to conveniently analyze. Alternatively, if the interior diameters are too small the core will contain a higher proportion of leaves to stem than is present in the volume of hay as a whole, thus providing inaccurate samples.

Importantly, the diameter indicated at $D_1$ should always be less than the diameter indicated at $D_2$. By maintaining the diameter of intake end 124 of hollow tube member 102 less than the diameter of the remainder of tube member 102, significant problems resulting from the plugging and binding of the hay core within tube member 102 are avoided. In this regard, it will be appreciated that hollow tube member 102 could also have a continuously tapered configuration in order to achieve nearly the same result. However, the structure illustrated and described in connection with FIGS. 1–4 has been found to work very well.

Furthermore, the outside diameter of hollow tube 102 should not be too much greater than interior diameter $D_1$ or binding may result as the embodiment is rotated and drawn into the bale. As explained earlier, the major difficulty of those devices available in the prior art is that they are often so difficult or inconvenient to use that the operator becomes tired or frustrated after obtaining only a few cores and then quits. Thus, the required number of cores to obtain a representative sample are not taken and the nutritive analysis of the hay may be inaccurate.

A major point which causes fatigue of the operator when using the devices found in the prior art is the effort required to push and pull the device into or out of the volume of hay. The present invention greatly reduces the effort required to insert and withdraw the device from the bail of hay due to the addition of a spiral ridge, also referred to as a screw member, functioning as a screw thread, marked 116 in FIG. 1.

In the embodiment illustrated in FIGS. 1–4, and as best illustrated in FIG. 1, the screw member is a spiral ridge, or thread, 116 attached to the exterior diameter of tube member 102. It will be appreciated that many different structures could be used for the screw member 116. For example, the length of the ridge, the height and width of the ridge, and the distance between the adjacent ridges (referred to as the pitch), may be varied as well as other alterations to the structure shown in FIG. 1.

In use, spiral ridge 116 acts as a screw thread and is provided with a sharpened engaging portion 118 as can be seen in FIG. 1. Engaging portion 118 of spiral ridge 116 facilitates cutting into the volume of hay. As embodiment 100 is rotated about the axis of the tube member 102, which is preferably by means of a hand brace 150 as shown in FIG. 3, spiral ridge 116, or other appropriate screw or auger-like structure serving the same function as the structure shown in FIG. 1, engages the volume of hay and, according to the direction of rotation, causes tube member 102 to be drawn into the volume of hay or to be withdrawn from the volume of hay.

It will be appreciated that many rotation implements other than hand brace 150 may be used to rotate the embodiment. For example, while generally not necessary, various power rotation implements, such as power drills, may be used. By incorporating spiral ridge 116 on tube member 102, the present invention may be used repetitively by the operator to obtain many samples without becoming fatigued.

It will be appreciated by those skilled in the art that many different materials may be used to fabricate spiral ridge 116 and that many methods may be used to form or attach spiral ridge 116 to the exterior of tube member. The pitch, or distance between corresponding points on adjacent threads measured parallel to the axis of tube member 102, may be in the range from about ¾ inch to about 1½ inches when the device is to be operated manually. Also, it is presently preferred that the ridge itself be about 3/16 of an inch wide and extend from the exterior surface of tube member 102 about the same distance.

However, in the case of a device to be used with a power rotation implement, it is preferred that the pitch be increased somewhere in the range from about 1½ inch to about 3 inches. Also, it is preferable that the height and width of ridge 116 be reduced. By increasing the pitch and decreasing the height of spiral ridge 116, the device is allowed to "slip" somewhat within the volume of hay as it is being rotated by the power rotation implement. In this way, the operator is able to control the speed and depth of penetration into the volume of hay when using a power rotation implement, even when the implement does not allow for rotation at a plurality of speeds.

Spiral ridge 116 should begin from a point proximal to intake end 124 on cutting tip 120 and extend some distance up toward discharge end 126 of tube member 102. However, while some applications may require more of the exterior diameter of tube member 102 to be provided with a spiral ridge, or other screw or auger-like structure, it is presently preferred that spiral ridge 116 occupy about one third of the length of tube member 102.

As shown in FIG. 2, at tube member discharge end, generally designated 126 in FIG. 1, a collection container 104 is mounted. In the embodiment illustrated in FIGS. 1-4, collection chamber 104, or collection container 104, is a generally cylindrical container. Collection container 104 is attached to tube member 102 such that tube member 102 discharges its contents through its discharge end 126 into the interior of collection container 104.

It will be appreciated that it is not necessary to the present invention that collection container 104 be attached to tube member 102 as shown in FIGS. 1-4. Rather, the present invention also encompasses embodiments without attached collection containers in which the hay core is removed directly from the tube member 102 and placed in a sample bag. Those skilled in the art will realize that there are many structures which could be used to attach either a manual or power rotation implement to tube member 102 in order that hay cores may be removed directly from the tube.

As can be seen in FIGS. 1 and 2, collection container 104 is provided with a lid 106. Collection container 104 of the embodiment illustrated in FIGS. 1 and 2 is attached to discharge end of tube member 102 by welding. Alternatively, collection container 104 may be attached by some detachable mechanism as will be explained later. In the embodiments illustrated in FIGS. 1-4, and as shown best in FIGS. 1 and 2, lid 106 is provided with a grasping post 110. Grasping post 110 in the embodiment illustrated in FIGS. 1 and 2 is welded to lid 106 so as to be in axial alignment with tube member 102. However, those skilled in the art will appreciate that other structures, such as a threaded nut (not shown) attached to lid 106 and a threaded grasping post (not shown) may also be used. The purpose of grasping post 110 is to allow a rotation implement to grasp and rotate embodiment 100.

It will be appreciated that grasping post 110 may be replaced with many structures other than that illustrated. For example, rather than a single grasping post, a handle could be directly attached to lid 106 for the user to grasp and by which the user could rotate the device. Also, many other structures could be used to allow connection of a rotation implement to the device. As shown in FIG. 3, the presently preferred rotation apparatus to be used in connection with the device is a hand brace 150. A hand brace may be connected to grasping post 110 by way of a chuck. The operator may then utilize hand brace 150 to easily rotate device 100 which is being inserted into a volume of hay. In FIG. 3 a bale of hay is partially shown at 160.

FIG. 3 shows the device being used to obtain a sample from bale 160. The operator's hands are shown rotating the device by use of a hand brace 150. Once the device has been inserted to an appropriate depth, which depends upon the size of a volume of hay, the direction of rotation is reversed and tube member 102 may be easily withdrawn from the volume of hay.

Collection container 104 should be large enough to hold many individual cores. For example, collection container 104 may be about 3½ inches in diameter and about 8 inches in length. Using these dimensions, the collection container's interior volume is large enough to hold approximately 20 hay cores.

When it is desired to remove the hay sample from collection container 104, lid 106 may be removed as shown in FIG. 4. As can be seen in FIG. 4, lid 106 is an oval shape. The oval shape is to accommodate slots 132 which are engaged by pivoting bolts 112, which are attached to the sides of collection container 104 and wing nuts 114.

Lid 106 is also provided with a key 130 and collection container 104 is provided with two key ways 134. When lid 106 is installed on collection container 104 such that key 130 engages key ways 134, and pivoting bolts 112 are placed in slots 132 and nuts 114 are tightened, as partially shown in FIG. 1, lid 106 is securely attached to collection container 104 such that any torsional rotation of lid 106 is transferred to collection container 104 and tube member 102 without exerting any undue stress on pivoting bolts 112.

Generally, as successive cores are taken, the new core will cause the old sample to be forced out of tube member 102 and into collection container 104. However, it may be desired that the last hay core also be moved into collection container 104 so that it can be included in the sample to be analyzed. In order to facilitate removing the last taken hay core from tube member 102, a rod 170 in FIG. 4, or other similar device may be used to push the material in tube member 102 into collection container 104.

Figure 5:
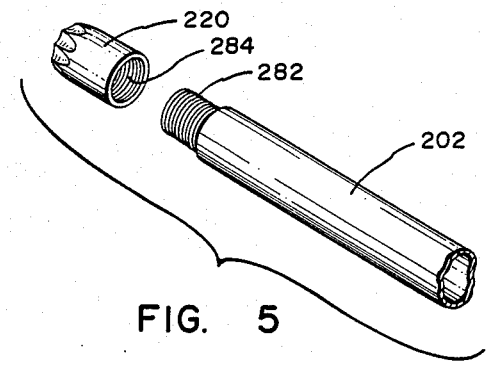
FIG. 5 is a perspective view of a portion of another preferred embodiment showing the removable cutting tip.

As mentioned earlier, it may be desirable to provide the hollow tube member with a removable cutting tip. However, it should be appreciated that resharpenable cutting tip 120 will not need to be replaced under normal circumstances. FIG. 5 partially shows an embodiment in which the resharpenable cutting tip 220 may be removed from hollow tube member 202 if necessary due to damage. In the embodiment illustrated in FIG. 5, removable cutting tip 220 is attached to the hollow tube member 202 by way of threads 282 provided on the exterior of tube member 202 and threads 284 provided on the interior circumference of removable cutting tip 220.

Similar to the previously described embodiment, removable cutting tip is preferably provided with a serrated cutting edge. Removable cutting tip 220 may be conveniently threaded onto, or off from, tube member 202. It will be appreciated by those skilled in the art that many different structures could be used to provide a removable cutting tip. By providing a removable cutting tip 220, the cutting tip may be easily replaced if it becomes damaged or if it is desired to resharpen cutting tip 220 while it is removed from tube member 202.

Figure 6:
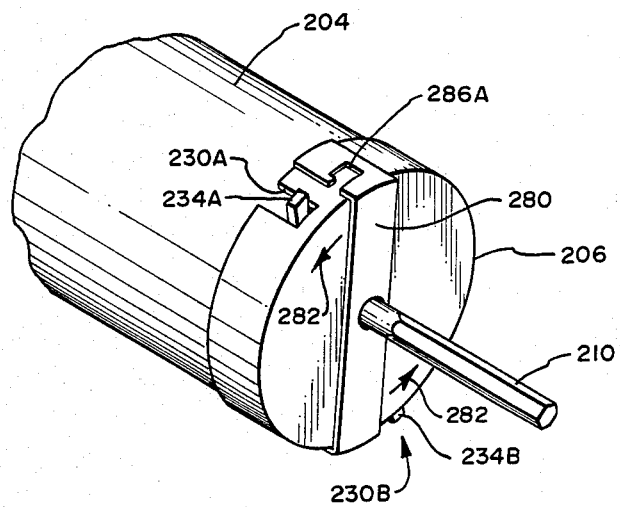
FIG. 6 is a perspective view of a portion of another preferred embodiment showing the collection container lid.

In FIG. 6, an embodiment is partially illustrated in which another structure is used in order to removably attach lid 206 to collection container 204. Rather than a key 130 in key way 134, as illustrated in FIG. 4, the embodiment illustrated in FIG. 6 is provided with two locking pins 234 provided on the outer circumference of collection container 204. Also, lid 206 is provided with two corresponding slots 230 which, when lid 206 is placed on collection container 204, engage locking pins 234. (Only one slot 230A, is visible in FIG. 6.) This provides that as grasping post 210, which is attached to lid 206, is rotated, collection container 204 and the device also rotate.

In order to secure lid 206 on collection container 204, locking arm 280 is provided. Locking arm 280 rotates about grasping post 210 and is provided with a notch 286 (only one of which 286A, is visible in FIG. 6) to engage locking pins 234. By rotating locking arm in the directions indicated by arrows 282, lid 206 may be selectively secured to, or freed from, collection container 204.

Figure 7:
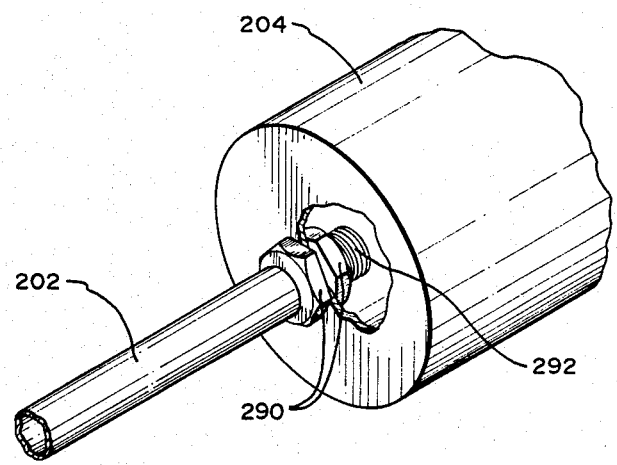
FIG. 7 is a partially cut away perspective view of a portion of another preferred embodiment showing the removable hollow tube.

FIG. 7 is a partial view of another preferred embodiment. FIG. 7 shows the discharge end of tube member 202 and also collection container 204 which is similar to designs known to those skilled in the art and which may be incorporated into the present invention. In the embodiment illustrated in FIG. 7, hollow tube member 202 may be detached from collection container 204. This may be desirable in order that different lengths of tube members 202 may be attached to collection container 204 if needed for taking cores from various sized bales, rolls, or stacks. In the embodiment illustrated in FIG. 7, tube member 202 is removed from collection container 204 by removing nuts 290 from the threaded portion 292 of tube member 202.

It will be appreciated by those skilled in the art that many structures other than that shown in FIG. 7 may be used to provide detachable tube members. For example, tube member 202 may be threaded directly into threads provided on collection container 204 (not shown in the figures). Also, in such a case it may be desirable to provide tube member extensions (also not shown in the figures) which would thread into both tube member 202 and collection container 204 to provide additional length to tube member 202.

As will be appreciated from the foregoing description, the present invention provides a device which allows for the efficient and easy collection of samples from volumes of hay. The present invention may be used with any volume of hay, including baled, rolled, stacked, or loose hay. When using the present invention with loose hay it is often helpful for the user to stand on the volume of hay so as to somewhat compress it. The present invention has the advantage of being of relatively sturdy and simple construction. Further, the structure of the present invention allows the user to obtain many cores without becoming fatigued or tired. This is facilitated by the cutting tip at the intake end of the tube member and the screw member which is associated with the tube member.

Thus, the difficulties which are inherent in the devices found in the prior art are overcome and a long felt need in the art has been satisfied. The device may be easily operated by a manual rotation implement, thus eliminating the necessity of obtaining a power source for a motor. Alternatively, embodiments may be fabricated which are particularly suited for use within a power rotation implement. Furthermore, a collection container is provided so that it will hold several samplings. Once removal of the sampled hay is desired, it is a simple matter to remove the lid to the collection container and transfer the contents to a sample bag. However, it may be desirable in some cases to eliminate the collection container and remove the hay cores directly from the hollow tube.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A device for taking a core from a volume of hay comprising:
    a hollow tube member having an intake end and a discharge end wherein the interior diameter of the intake end is of a first diameter which is less than any other interior diameter of the hollow tube member such that the core is allowed to pass from the intake end to the discharge end of the hollow tube member without binding;
    a removable, serrated cutting edge, comprising a material which is resharpenable, located around the perimeter of the intake end of the hollow tube member;
    screw means disposed about the outer surface of the hollow tube member, the screw means comprising at least one ridge protruding from the outer surface of the hollow tube member and forming a spiral from a first location in proximity to the intake end to a location less than about half the length of the hollow tube member;
    means for attaching a rotation implement to the device such that as the rotation implement alternately rotates in a clockwise and counterclockwise direction, the hollow tube and screw means also rotate in the same direction and, according to the direction of rotation, the hollow tube may be selectively drawn into and out of the volume of hay whereby a hay core is gathered by the hollow tube member; and
    a collection container removably attached to the discharge end of the hollow tube member, the collection container being adapted to collect the hay core which is gathered into the hollow tube member, the collection container being substantially cylindrical and being closable by a substantially disk shaped lid having a key protuding from, and extending substantially diametrically along, the surface thereof that in use is adjacent to the interior of the collection container, and key way means provided in the collection container cylindrical side wall and adapted to receive the key.

2. A device for taking a core from a volume of hay as defined in claim 1 wherein the first diameter is in the range from about ¼ inch to about ¾ inch.

3. A device for taking a core from a volume of hay as defined in claim 2 wherein the diameter of the hollow tube member other than the first diameter is in the range from 5/16 of an inch to 1¼ inches.

4. A device for taking a core from a volume of hay as defined in claim 1, wherein the pitch of the spiral ridge being in the range from ¾ inch to about 1½ inches.

5. A device for taking a core from a volume of hay as defined in claim 1 wherein the length of the hollow tube member is in the range from about 12 inches to about 4 feet.

6. A device for taking a core from a volume of hay as defined in claim 1 further comprising means in addition to said key and key way means for securing the lid on the end of the collection container opposite the discharge end of the hollow tube member.

7. A device for taking a core from a volume of hay as defined in claim 6, wherein said key way means comprises two key ways formed on the collection container, the key ways being positioned opposite of each other, the key positioned on the lid so as to be capable of engaging both key ways and transferring any rotational motion of the lid to the collection container.

8. A device for taking a core from a volume of hay as defined in claim 1 wherein the means for attaching a rotation implement comprises a post in axial alignment with the hollow tube member.

9. A device for taking a core from a volume of hay as defined in claim 1 wherein the rotation implement is power-driven.

10. A device for taking a core from a volume of hay as defined in claim 9 wherein the pitch of the screw means is in the range from about 1½ inches to about 3 inches.

11. A device for taking a core from a volume of hay as defined in claim 1 wherein the rotation implement is a hand brace.

12. A device for obtaining a sample of hay from a volume of hay comprising:

a hollow member, the hollow tube member having a length in the range from about 12 inches to about 4 feet and an intake end and a discharge end, the intake end comprising an interior diameter equal to a first dimension and the remainder of the hollow tube member having an interior diameter equal to a second dimension, the first dimension being in the range form about ¼ inch to about ¾ inch and less than the second dimension, the second dimension being in the range from bout 5/16 inch to about 1¼ inches such that the sample of hay is allowed to pass from the intake end to the discharge end of the hollow tube member;

a cylindrical collection container attached to the hollow tube at its discharge end, the collection container adapted to receive a hay core from the hollow tube member, the collection container being removable from the hollow tube member and comprising a substantially disk shaped lid having a key protruding from, and extending substantially diametrically along, the surface thereof that in use is adjacent to the interior of the container and a key way provided in the collection container cylindrical side wall and adapted to receive the key;

a serrated cutting edge, comprising a material which is resharpenable, located around the perimeter of the intake end, the cutting edge adapted to cut the hay as the hollow tube is rotated about its axis, the serrated cutting edge being positioned on a removable cutting tip;

a spiral ridge mounted on the exterior of the hollow tube member and acting as a screw member, the spiral ridge beginning in proximity to the serrated cutting edge and extending along less than about half of the hollow tube member, the pitch of the spiral ridge being in the range from about ¾ inch to about 1½ inches; and a grasping post mounted in axial alignment with the axis of the hollow tube member, the grasping post adapted to be grasped by a rotation implement selectively rotating in clockwise and counterclockwise directions such that a user of the device may selectively rotate the hollow tube in the same direction causing the spiral ridge to engage the volume of hay and drawing the hollow tube into the hay and alternatively withdrawing the hollow tube, whereby a hay core is taken up by the hollow tube and may be deposited in the collection container.

* * * * *

UNITED STATES PATENT AND TRADEMARK OFFICE
CERTIFICATE OF CORRECTION

PATENT NO. : 4,827,776
DATED : May 9, 1989
INVENTOR(S) : Jody A. Gale et al.

It is certified that error appears in the above-identified patent and that said Letters Patent is hereby corrected as shown below:

Column 8, lines 42-43, "tube member." should be --tube member 102.--

Column 10, line 42, "removable cutting tip" should be --removable cutting tip 220--

Column 13, line 26, "form" should be --from--

Signed and Sealed this

Twelfth Day of June, 1990

Attest:

HARRY F. MANBECK, JR.

*Attesting Officer*    Commissioner of Patents and Trademarks